United States Patent [19]

Hutchison et al.

[11] Patent Number: 4,948,523

[45] Date of Patent: * Aug. 14, 1990

[54] CHLORINE-FREE SILVER PROTECTIVE LUBRICANT COMPOSITION (I)

[75] Inventors: David A. Hutchison, Naperville; Lionel D. Moore, Lisle, both of Ill.

[73] Assignee: Amoco Corporation, Chicago, Ill.

[*] Notice: The portion of the term of this patent subsequent to Oct. 3, 2006 has been disclaimed.

[21] Appl. No.: 103,186

[22] Filed: Sep. 30, 1987

[51] Int. Cl.$^5$ .............. C10M 105/22; C10M 105/58
[52] U.S. Cl. .................................................. 252/47
[58] Field of Search ............... 252/47, 47.5, 33, 56 R

[56] References Cited

U.S. PATENT DOCUMENTS

| | | | |
|---|---|---|---|
| 2,685,588 | 8/1954 | Goshern | 252/47 |
| 2,690,999 | 10/1954 | Lowe | 252/47 |
| 2,765,289 | 10/1956 | Fields | 252/47 |
| 2,910,439 | 10/1959 | Fields | 252/47 |
| 2,956,020 | 10/1960 | Suprin et al. | 252/33.4 |
| 3,110,673 | 11/1963 | Benoit | 252/51.5 |
| 3,281,358 | 10/1966 | Furey | 252/34 |
| 3,341,542 | 9/1967 | LeSuer et al. | 260/268 |
| 3,405,064 | 10/1968 | Miller | 252/51.5 |
| 4,104,179 | 8/1978 | Colclongh | 252/47 X |
| 4,263,015 | 4/1981 | Sung et al. | 44/63 |
| 4,280,916 | 7/1981 | Richards | 252/33.4 |
| 4,282,007 | 8/1981 | Sung | 44/53 |
| 4,283,296 | 8/1981 | Nebzydoski et al. | 252/49.9 |
| 4,388,198 | 6/1983 | Butcosk | 252/28 |
| 4,491,527 | 1/1985 | Lange et al. | 252/51.5 A |
| 4,734,257 | 3/1988 | Penninger | 252/392 X |

FOREIGN PATENT DOCUMENTS

| | | |
|---|---|---|
| 0024146 | 2/1981 | European Pat. Off. . |
| 225580 | 6/1987 | European Pat. Off. . |
| 1121316 | 6/1959 | France . |
| 2185265 | 7/1987 | United Kingdom . |

*Primary Examiner*—William R. Dixon, Jr.
*Assistant Examiner*—James M. Hunter, Jr.
*Attorney, Agent, or Firm*—Matthew R. Hooper; William H. Magidson; Ralph C. Medhurst

[57] ABSTRACT

A lubricating composition, preferably essentially free of zinc dihydrocarbyldithiophosphate compounds, and optionally free of chlorine containing silver lubricity agents, comprising a major proportion of an oil of lubricating viscosity and a minor amount of a silver protective agent comprising the reaction product of a $C_5$ to $C_{60}$ carboxylic acid and at least one amine selected from the group consisting of (1) guanidine, urea, and thioruea compounds; (2) $C_1$ to $C_{20}$ hydrocarbyl or hydroxy-substituted hydrocarbyl mono-amines, alkylene diamines, and (3) polyalkylene polyamines; and N-alkyl glycine.

33 Claims, No Drawings

CHLORINE-FREE SILVER PROTECTIVE LUBRICANT COMPOSITION (I)

BACKGROUND OF THE INVENTION

1. Field of the Invention

The present invention relates generally to lubricant compositions useful in medium speed diesel engines, such as commonly found in railroad locomotives, marine towboats and stationary power applications. These engines frequently have silver bearings which necessitate lubricant compositions incorporating specialized silver protective agents to protect against wear, extreme pressure and corrosion of silver parts. However, it is well known that zinc-containing wear agents such as zinc dihydrocarbyldithiophosphates (typically used in passenger cars) cannot be used for this purpose given their incompatibility with silver bearings. It is also desirable to find alternatives to chlorine containing silver lubricity agents widely used in the art for silver protection. Thus, the present invention, more particularly, is directed to a lubricating composition, preferably essentially free of zinc dihydrocarbyldithiophosphate compounds, and optionally free of chlorine containing silver lubricity agents, comprising a major proportion of an oil of lubricating viscosity and a minor amount of a silver protective agent comprising the reaction product of a $C_5$ to $C_{60}$ carboxylic acid and at least one amine selected from the group consisting of (1) guanidine, urea, and thiourea compounds; (2) $C_1$ to $C_{20}$ hydrocarbyl or hydroxy-substituted hydrocarbyl mono-amines, alkylene diamines, and (3) polyalkylene polyamines; and N-alkyl glycine. A preferred guanidine reactant is aminoguanidine, or its salts, such as, preferably, aminoguanidine bicarbonate; a preferred alkylene diamine reactant is ethylenediamine; and a preferred N-alkyl glycine is N-methyl glycine. Preferred carboxylic acid-amine reaction products based upon guanidine are the aminoguanidine fatty acid amides and the corresponding 1,2,4-triazole-3-amines, in particular, aminoguanidine monooleamide and oleyl-1H-1,2,4-triazole3-amine. Preferred carboxylic acid-amine reaction products using an alkylene diamine as the amine reactant are the fatty acid imidazolines. Preferred carboxylic acid-amine reaction products using N-alkyl glycine as the amine are the fatty acid amides of N-methyl glycine.

The invention is further directed to a method for protecting silver parts in an internal combustion engine by lubricating the same with a lubricant composition comprising a major proportion of an oil of lubricating viscosity and a minor amount of at least one of the above-mentioned silver protective additives.

In a further aspect of the invention, the above silver protective additives are found to work in synergy with organo-sulfur compounds, preferably thiadiazole compounds selected from the group consisting of
 (a) 2,5-dimercapto-1,3,4-thiadiazoles,
 (b) 2-(mercapto)-5-(hydrocarbylthio)-1,3,4-thiadiazoles,
 (c) 2,5-bis-(hydrocarbylthio)-1,3,4-thiadiazoles,
 (d) 2,5-bis-(hydrocarbyldithio)-1,3,4-thiadiazoles and
 (e) 2,5-bis(hydrocarbyldithio)-1,3,4-thiadiazole.

Thus, the invention is further directed to silver protective lubricant compositions comprising organo-sulfur compounds in combination with the above-mentioned carboxylic acid-amine reaction products, as well as to a method for protecting silver engine parts which utilize such synergistic combinations.

2. Discussion of the Prior Art

Large numbers of medium speed diesel engines in the United States, as well as other countries, utilize silver-plated bearings. Thus, apart from providing stability against oxidation and protection against the formation of sludge and carbonaceous deposits, crankcase lubricating oils intended for use in medium speed diesel engines must also be formulated with specialized silver protecting agents in order that silver parts in the engine are not attacked either by the additives in the oil or by the dispersed neutralized decomposition products produced during extended engine operation. Such agents, often referred to as silver lubricity agents, protect against extreme pressure, wear and corrosion.

Although it is essential to include a silver lubricity agent in diesel oils intended for use in engines having silver parts, it is well known that such oils must exclude the zinc-containing anti-wear agents mentioned above, such as the zinc dihydrocarbyldithiophosphates, given the known propensity of the latter to damage the silver components of diesel engines. This is explained, for example, in U.S. Pat. No. 4,428,850 (column 1, lines 63–68).

The antagonism between zinc-containing wear inhibitors and the silver parts in diesel engines has been circumvented in the prior art by using alternative silver lubricity compounds, the most common of which are the chlorinated hydrocarbons such as shown in Sung, U.S. Pat. No. 4,171,269. However, while the chlorine compounds of the prior art have been shown to be effective in protecting the silver parts of diesel engines, the Occupational Safety and Health Administration in the United States and other public health agencies throughout the world have expressed concern over potential biological effects of chlorinated compounds. Therefore, an incentive exists to develop novel compositions effective in protecting the silver parts of medium speed diesel engines which overcome the problems or potential problems encountered with the zinc-containing and chlorine-containing wear inhibitors.

A related problem in obtaining silver protection in lubricant compositions is that overbased alkali and alkaline earth metal detergents, added to provide beneficial cleanliness properties to lubricant formulations, at the same time produce deleterious side effects on silver parts. Thus, while it is desirable to impart a high degree of alkalinity through the use of overbased detergents, such overbased materials tend to impair the silver protection characteristics of the oil, making it difficult to formulate a diesel lubricant composition which gives the desired level of cleanliness, yet at the same time protects the silver parts of the diesel engine. Therefore, a need exists for diesel lubricant additive compositions which not only protect the silver parts of the diesel engine, but also operate so as to render the lubricant composition tolerant to markedly higher levels of overbased detergents.

A number of patents are thought to be of relevance as background to the compositions and methods described in the present invention but do not address expressly, or even inherently, the problems described above. For example, Andress, U.S. Pat. No. 3,655,560, describes antioxidants and metal deactivators for fuel oils, lubricating oils and greases which are compounds selected from the group consisting of ketimines of aminoguanidine, aldimines of ketimines of aminoguanidine and aldimines of amides of aminoguanidine. This patent does not disclose or suggest the reaction product of a carboxylic acid with aminoguanidine as a silver lubricity agent in diesel lubricant formulations, as taught in the present invention.

Another patent relating to aminoguanidine in lubricant compositions is Frangatos, U.S. Pat. No. 4,295,982 which discloses products from aminoguanidines (or their salts), monocarboxylic acids and sulfur and their use as anti-rust and anti-corrosion additives. The compounds of this patent differ from those of the present invention insofar as sulfur is not used in the preparation of the compositions of the present invention. Moreover, Frangatos is not directed to the attainment of silver lubricity in diesel engines.

Knepper, et al., U.S. Pat. No. 4,595,523, is directed to a corrosion inhibiting composition comprising a triazole and an amine salt of an acid. While the patent states that "any amine which would form an acid salt which is soluble in an alcohol and inhibits corrosion may be used in the invention," there is no specific disclosure of carboxylic acid salts of aminoguanidine. Also, the invention of Knepper is clearly directed to a composition which is added to an alcohol fuel. Thus, the patent in no way relates to a lubricant composition, free of zinc compounds, which would be suitable for addition to a diesel engine lubricating composition used in a diesel engine having silver bearings.

Boehringer, et al., U.S. Pat. No. 3,749,702, describes metal deactivators useful as additives in lubricants and, more particularly, describes salts formed from amides prepared from benzoic acid or a substituted benzoic acid and aminoguanidine bicarbonate and an aliphatic or aromatic carboxylic acid. The present invention is not directed to the reaction product of a benzoic acid or its derivatives and aminoguanidine bicarbonate and is clearly distinguishable from Boeheringer, et al.

Biswell, U.S. Pat. No. 2,584,784, describes the higher aliphatic salts of 1-salicylalaminoguanidine as antioxidant additives. Representative acids which may be employed to form the salts in Biswell include oleic acid. Like the patents discussed above, Biswell is distinguishable from the present invention because it does not disclose the reaction product of carboxylic acids and aminoguanidine and is not directed to silver protection in diesel engine lubricants.

U.K. Patent Specification No. 1,440,129 discloses metal passivators used to reduce the corrosion of engine component materials such as copper and lead which include condensation products of salicylaldehyde with hydrazine derivatives and the $C_{12}$–$C_{18}$ fatty acid salts of such condensation products such as the oleic acid salt of salicylalaminoguanidine, preferably the monooleic salt. The patent goes on to discuss useful load-carrying additives (extreme pressure agents) including zinc dihydrocarbyl dithiophosphates. Given the inclusion of zinc-containing wear agents in its discussion of wear inhibitors, the British Patent Specification is clearly not directed to lubricating compositions for diesel engines containing silver parts.

Lange, et al., U.S. Pat. No. 4,491,527, describes ester-heterocycle compositions useful as "lead paint" inhibitors in lubricants. In particular, at column 4, lines 34–51 (plus the accompanying drawings) the patentee describes the reaction of a substituted carboxylic acid (e.g., polybutylsuccinic acid) with an acyclic heterocycle precursor which cyclizes with the carboxylic acid group to form a heterocyclic compound. An illustrative acyclic heterocycle precursor which may react with an acid or an acid derivative group to form such heterocycles include aminoguanidine and salts thereof, semicarbazide, thiosemicarbazide, carbohydrazide and thiocarbohydrazide, as well as salts thereof such as aminoguanidine bicarbonate. Thus, the composition of Lange, et al. can include the 5-(polyalkenylsuccinic)-3-amino-1,2,4-triazole. The patent, however, is not specifically directed to a lubricant composition for use in diesel engines having silver parts. In fact, at column 12 of the patent, an illustrative lubricant composition of the invention is shown to include a zinc dialkylphosphorodithioate wear inhibitor which would be totally unacceptable in the present invention.

Sung, et al., U.S. Pat. No. 4,256,595, is directed to a diesel crankcase lubricant composition comprising a lubricating oil base and the reaction product of a hydrocarbyl succinic anhydride in which the hydrocarbyl radical has from 12 to 30 carbon atoms, and 5-aminotriazole. The background section of the patent states that it is known to employ a thiadiazole as a corrosion inhibitor for diesel crankcase lubricating oil. The patent, however, does not disclose or suggest a synergistic combination of 3-amino-1,2,4-triazole compounds and 1,3,4-thiadiazole compounds, as disclosed in the present invention.

Davis, U.S. Pat. No. 4,136,043, is directed to compositions useful for suppression of copper activity and "lead paint" deposition and lubricants. The compositions are produced by preparing a mixture of an oil soluble dispersant (preferably a substantially neutral or acidic carboxylic dispersant) and a dimercaptothiadiazole, preferably 2,5-dimercapto-1,3,4-thiadiazole. As stated at column 4, lines 24–39, the carboxylic dispersants encompass nitrogen bridged dispersants wherein the nitrogen group is derived from aliphatic, aromatic, heterocyclic and carbocyclic amines as well as substituted ureas, thioureas, hydrazines, guanidines, amidines, amides, thioamides, cyanamides and the like. Davis is not directed to the achievement of silver lubricity in lubricating compositions for diesel engines.

SUMMARY OF THE INVENTION

In view of the problems cited earlier, a general object of the present invention is to provide a silver protective lubricant additive composition.

A further object of the invention is to provide a silver protective lubricant additive composition suitable for addition to lubricant compositions used to lubricate the moving parts of medium speed diesel engines such as found in railway locomotives, marine towboats and stationary power applications.

Another object of the invention is to provide a silver lubricity additive composition suitable for addition to lubricating compositions used to lubricate the moving parts of medium speed diesel engines, which additive composition provides enhanced protection against silver wear, corrosion and extreme pressure.

Yet another object of the invention is to provide a lubricating composition that can tolerate higher levels of alkalinity (for cleanliness) without a concomitant increase in damage to silver engine parts.

Still another object of the present invention is to provide a synergistic silver protective additive composition suitable for addition to lubricating compositions used in engines having silver parts, wherein the synergistic properties of such composition are evident from increased silver protection at reduced additive treat rates. Other objects appear hereinafter.

We have now found that the foregoing objects are provided for in the present invention, namely, a lubricating composition preferably essentially free of zinc-containing wear inhibitor compounds and comprising a major proportion of an oil of lubricating viscosity and a minor amount of a silver protective additive composition, the latter comprising at least one member selected from the group consisting of the reaction product of a $C_5$ to $C_{60}$ aliphatic carboxylic acid and at least one amine selected from the group consisting of (1) guanidine, urea, and thiourea compounds; (2) $C_1$ to $C_{20}$ hydrocarbyl mono-amines, alkylene diamines, and polyalkylene polyamines; and (3) N-alkyl glycine. Preferably, the silver protective additive composition comprises at least one member selected from the group consisting of:

(A) the reaction product of a $C_5$ to $C_{60}$ aliphatic carboxylic acid and (i) guanidine, urea or thiourea compounds having the general formula:

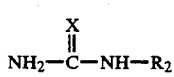

wherein X is $NR_1$, O, or S, and $R_1$ is H or $C_1$ to $C_{15}$ hydrocarbyl, and $R_2$ is H, —NR'R'' or $C_1$ to $C_{20}$ hydrocarbyl or hydroxy-substituted hydrocarbyl and R' and R'' (being the same or different) are H or $C_1$ to $C_{20}$ hydrocarbyl or hydroxy-substituted hydrocarbyl;

or (ii) salts of said compounds;

(B) the reaction product of a $C_5$ to $C_{60}$ aliphatic carboxylic acid and at least one amine selected from the group consisting of (i) mono-amines having the general formula HNRR' where R and R' (being the same or different) are H, or $C_1$ to $C_{20}$ hydrocarbyl or hydroxy-substituted hydrocarbyl; (ii) alkylene diamines having the formula:

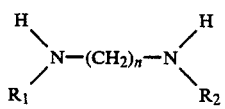

wherein n=2 to 10, and $R_1$ and $R_2$ (the same or different) are H or $C_1$ to $C_{20}$ hydrocarbyl or hydroxy-substituted hydrocarbyl; and (iii) polyalkylene polyamines having the general formula:

wherein A is a divalent alkylene radical having 2 to 6 carbons, x is an integer from 1 to 10, and R is H or $C_1$ to $C_{20}$ hydrocarbyl or hydroxy substituted hydrocarbyl;

(C) the reaction product of a $C_5$ to $C_{60}$ aliphatic carboxylic acid and derivatives of glycine having the general formula:

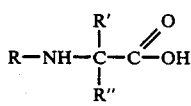

wherein R=H or $C_1$ to $C_{20}$ hydrocarbyl or hydroxy-substituted hydrocarbyl; and R' and R'' (the same or different) are H or $C_1$ to $C_{20}$ hydrocarbyl.

The invention is further directed to a lubricant oil composition comprising a major proportion of an oil of lubricating viscosity and a minor amount of a silver protective additive composition comprising the combination of (I) an organo sulfur compound, preferably a thiadiazole compound having the general formula:

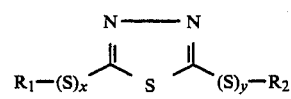

wherein x and y (the same or different) are integers from 1 to 5 and $R_1$ and $R_2$ (the same or different) are H, or $C_1$ to $C_{60}$ hydrocarbyl;

and (II) at least one of the silver protective agents described in parts (A) through (C) of the preceding paragraph.

As a method, the invention is directed to the protection of silver engine parts in an internal combustion engine by lubrication thereof with the above-described lubricating compositions.

A primary advantage in the silver protective agents (or combinations thereof) prescribed for use in the lubricating compositions of the present invention, particularly in the context of medium speed railway diesel engines, is the fact that such agents are surprisingly effective substitutes for the chlorine-containing silver lubricity agents mentioned earlier which, heretofore, have been virtually a staple additive for providing silver lubricity in the context of medium speed diesel engines. The most frequently used chlorine-containing agents are the chlorinated paraffins such as the commercial product "Chlorowax."

A further advantage of the present invention is an unexpected and pronounced synergistic effect observed in lubricating compositions according to the present invention which comprise the inventive combination of an organo-sulfur compound and at least one of the silver protective agents selected from (A) through (C) above. The synergistic action of the combination is noted in that the silver protection afforded by any one of the additives (A) through (C), alone, or that afforded by the sulfur-containing compound, alone, can be significantly enhanced if these materials are used in combination in the lubricant compositions of the present invention. Such enhancement allows a lower treat rate of the synergistic combination needed to achieve a desired level of passing silver protection than would otherwise be required if either member of the combination were to be used alone.

Another important advantage in the present invention is that lubricating compositions incorporating the above-mentioned agents have been found to have a much higher tolerance, in terms of silver protection, toward overbased detergents, in particular the overbased calcium phenates. While it is known that overbased detergents are harmful to the silver bearings in medium speed diesel engines, the lubricant compositions of the present invention surprisingly can accommodate at least twice the amount of overbased phenate as ordinarily could be tolerated in conventional lubricating formulations which incorporate the prior art chlorine-containing silver lubricity agents. Thus, in accordance with the present invention, lubricating compositions for medium speed diesel engines having silver parts can be formulated with much greater cleanliness characteristics without an ensuing loss of silver protection.

In addition to the above-stated advantages, the compositions of the present invention are extremely effective metal passivators, particularly with respect to copper and lead, as measured by superior oxidation performance.

DETAILED DESCRIPTION

Generally speaking, the silver protective additives prescribed for use in the lubricating compositions of the present invention can be obtained by reacting in a conventional manner a $C_5$ to $C_{60}$ aliphatic carboxylic acid and an amine selected from the group consisting of (1) guanidine, urea and thiourea compounds; (2) hydrocarbyl or hydroxysubstituted hydrocarbyl monoamines, alkylene diamines, and polyalkylene polyamines; and (3) N-alkyl glycine, to obtain reaction products comprising amides and/or heterocylic derivatives thereof such as the triazoles and imidazolines. If desired, the above carboxylic acid-amine reaction products may be used in synergistic combination with an organo sulfur compound, preferably thiadiazoles having the formula set out above.

In somewhat greater detail silver protective additive (A) can be prepared by reacting under relatively mild conditions said guanidine, urea or thiourea compound as defined earlier, or the salts of such, with a $C_5$ to $C_{60}$ aliphatic carboxylic acid. Preferred for use in the present invention are the inorganic salts of guanidine compounds wherein the anion is halide, carbonate, nitrate, phosphate, orthophosphate, etc. A particularly preferred guanidine derivative for the preparation of silver protective additive agent (A) used in the present invention is aminoguanidine bicarbonate.

Guanidine, urea, and thiourea compounds used in the present invention such as the preferred aminoguanidine bicarbonate, are readily obtainable from commercial sources or can be prepared in a well-known manner.

To prepare silver protective additive (A) used in the lubricating compositions of the present invention, the guanidine, urea or thiourea compound, preferably aminoguanidine bicarbonate, can be reacted with a $C_5$ to $C_{60}$ aliphatic carboxylic acid in the temperature range of from about 65° C. to about 185° C.

Examples of suitable carboxylic acids include the saturated aliphatic monocarboxylic acids such as valeric caproic, caprylic, capric, lauric, myristic, palmitic, stearic arachidic, behenic, lignoceric, and the like; saturated aliphatic dicarboxylic acids such as glutaric, adipic, pimelic, suberic, azelaic, sebacic and the like; cycloaliphatic acids such as cyclohexane monocarboxylic acid and cyclohexane dicarboxylic acid; unsaturated aliphatic monocarboxylic acids such as decenoic, decendioic, undecenoic, tridecenoic, pentadecenoic, pentadecendienoic, heptadeceneoic, oleic, linoleic, linolenic ricinoleic and the like. If a dicarboxylic acid is used, then two moles of the aminoguanidine bicarbonate can react with the carboxylic acid.

Another type of $C_5$ to $C_{60}$ carboxylic acid useful in preparing the silver protection agents used in the present invention are the so-called dimer or dimerized fatty acids, preferably those containing conjugated unsaturation. The formation and structure of the dimer acids are shown in U.S. Pat. Nos. 3,180,832; 3,429,817 and 4,376,711, incorporated by reference. Commercially available dimer acids may contain as much as 25% trimer, and the use of such commercial mixtures is within the scope of the present invention.

Carboxylic acids suitable for use in making silver protecting additive (A) prescribed for use in the present invention include the commercially available fatty acids, or mixtures thereof, derived from corn oil, soybean oil, safflower oil, coconut oil, tall oil, tung oil, sunflower oil, rapeseed oil, cottonseed oil, peanut oil, palm kernel oil, linseed oil, olive oil, and castor oil, etc. Particularly preferred is a monocarboxylic unsaturated fatty acid of the formula:

$$R-CH_2-COOH$$

wherein R is an alkenyl group, an alkedienyl group or an alketrienyl group containing about 5 to 60 carbon atoms. That is to say, the R groups will contain one, two, or three double bonds. Examples of such acids useful for reaction with guanidine compounds according to the present invention are myristoleic acid, palmitoleic acid, oleic acid, ricinoleic linoleic acid, linolenic acid, eleostearic acid, elaidic acid, brassidic acid, arachidonic acid, abietic acid, and the like. Especially preferred is oleic acid. For purposes of the present invention, "oleic acid" means essentially neat oleic acid as well as commercially available oleic acid which, typically, comprises a major proportion of oleic acid in combination with lesser amounts of other fatty acids.

In the present invention, where the preparation of a reaction product calls for the reaction of a carboxylic acid, it should be understood that the term "carboxylic acid" encompasses reactive derivatives thereof such as the anhydrides, etc.

The reaction between the guanidine, urea or thiourea compound, preferably aminoguanidine bicarbonate, and the carboxylic acid, preferably oleic acid, is a condensation reaction. In carrying it out, the mole ratio of guanidine, urea or thiourea to acid can be in the range of about 0.7:1 to about 1.2:1, and is preferably 0.9:1 to about 1:1. The reaction product preferred for use as silver-protective additive (A) in the present invention is obtained by reacting aminoguanidine, preferably the bicarbonate, and oleic acid within a temperature range of from about 100° C. to about 182° C. and preferably from about 120° C. to about 145° C. Optimum yield can be obtained at these temperatures in from one hour to about eight to ten hours and preferably from about 1.5 to about 4 hours. The reaction can be carried out in a suitable solvent such as toluene and is preferably conducted in the presence of a small amount of anti-foamant due to vigorous foaming which can take place during the reaction.

The exact nature of the reaction product obtained upon reacting a carboxylic acid, preferably oleic acid, and aminoguanidine bicarbonate under the preferred reaction conditions is not well understood. However, the principle component of the reaction product is most likely aminoguanidine monooleamide having either of the following structures:

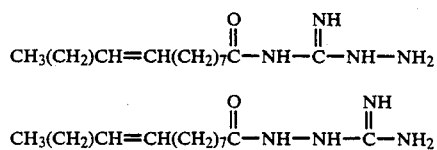

However, it is also likely that the reaction product includes minor proportions of other species, including without limitation the 1,2,4-triazole-3-amine having the formula:

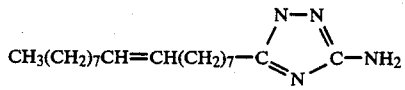

Accordingly, a preferred embodiment the silver protective additive agent (A) prescribed for use in the present invention, preferably obtained by reacting oleic acid with aminoguanidine bicarbonate, comprises predominantly aminoguanidine monooleamide but is likely to include also smaller varying amounts of the 1,2,4-triazole as well as other possible reaction products.

In regards to the reaction of a $C_5$ to $C_{60}$ carboxylic acid with aminoguanidine or its salts such as aminoguanidine bicarbonate, the reaction conditions, in particular the reaction temperature, can be modified such that the predominant reaction product is the 1,2,4-triazole-3-amine pictured above. Generally, the triazole is the predominant product if the reaction is carried out at temperatures greater than about 170° C.

Silver protection agent (B) prescribed for use in the present invention is the reaction product of a $C_5$ to $C_{60}$ carboxylic acid and at least one amine selected from the group consisting of (i) $C_1$ to $C_{20}$ hydrocarbyl or hydroxysubstituted hydrocarbyl mono-amines, (ii) $C_1$ to $C_{20}$ N-hydrocarbyl or N-hydroxy hydrocarbyl alkylene diamines; and (iii) $C_1$ to $C_{20}$ N-hydrocarbyl or N-hydroxyhydrocarbyl polyalkylene polyamines, the general formulas for which are set forth above in the Summary of the Invention. Suitable carboxylic acids are those which have been described for use in the preparation of silver protection (A) above. Preferred are the alkylene diamine fatty acid reaction products.

The reaction between the carboxylic acid and the above amines can be carried out at a temperature in the range of about 100° C to about 200° C. A preferred reaction temperature is about 100° C to about 200° C. The reaction can be carried out in an organic solvent such as toluene to facilitate the removal of water which is evolved by the reaction, or the reaction can take place in a diluent oil. See U.S. Pat. Nos. 2,267,965 or 2,214,152, incorporated by reference.

Preferred is the reaction of a carboxylic acid and ethylenediamine resulting in formation of an imidazoline having the following structure where R is the remainder of the carboxyl moiety:

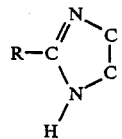

Other reaction products may be present in lesser amounts.

A silver protective additive (B), suitable for use in the present invention, can be obtained commercially. A particularly preferred product for use in the lubricating compositions of the present invention is available from Ciba-Geigy under the trade name "Amine O".

Silver protective additive (C) prescribed for use in the lubricating compositions and methods of the present invention is the reaction product of a $C_5$ to $C_{60}$ carboxylic acid or derivatives thereof with N-alkyl derivatives of glycine. The carboxylic acids suitable for use in preparing the reaction product (C) are the same carboxylic acids used in the preparation of silver protective additives (A) and (B) above. The preferred glycine derivative is N-methylglycine. The reaction between the carboxylic acid and the N-alkylglycine can be carried out in a conventional manner or one can obtain a suitable product from a commercial source. For example, the sodium salt of N-methylglycine can be reacted with the desired carboxylic acid or the acid chloride of the desired carboxylic acid at about 25° C. to about 50° C. in an organic solvent such as isopropanol in the presence of a stocihiometric amount of base, followed by neutralization of the reaction product with mineral acid. An acid/N-methyl glycine reaction acid product can be obtained commercially from Ciba-Geigy under the trade name "Sarkosyl O".

In addition to lubricating compositions comprising silver protecting amounts of the agents (A) through (C) discussed above, and lubricating methods utilizing such agents, the present invention is further directed to synergistic combinations of at least one of the silver protective agents selected from (A) to (C) above and an organo-sulfur compound. While any organo-sulfur compound can be used in the present invention, preferred are compounds selected from the group consisting of sulfurized olefins, sulfurized fatty acids and esters, sulfur-containing heterocyclic compounds, sulfurized hydroxy-aromatic compounds, disulfides, dithiocarbamates and thiadiazoles. Examples are 2-mercapto benzothiazole available from Vanderbilt under the tradename ROKON®, dibenzyl disulfide, and 4,4'-methylene bis(dibutyldithio)carbamate available from Vanderbilt under the tradename Vanlube®7723. Particularly preferred are the 2,5-dimercapto-1,3,4 thiadiazole, the 2-mercapto-5-hydrocarbyldithio-1,3,4-thiadiazole, the 2,5-bis(hydrocarbyldithio)-1,3,4-thiadiazole, 2-mercapto-5-hydrocarbyldithio-1,3,4-thiadiazole and the 2,5-bis(hydrocarbylthio)-1,3,4-thiadiazole. These compounds have the structural formulas shown below:

2,5-dimercapto-1,3,4-thiadiazole

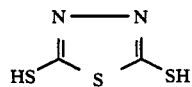

2-mercapto-5-hydrocarbylthio-1,3,4-thiadiazole

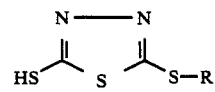

2-mercapto-5-hydrocarbyldithio-1,3,4-thiadiazole

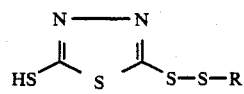

2,5-bis(hydrocarbyldithio)-1,3,4-thiadiazole

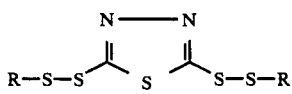

2,5-bis(hydrocarbylthio)-1,3,4-thiadiazole

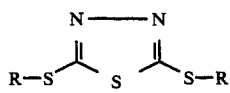

A particularly preferred 1,3,4-thiadiazole composition for use in the present invention is a mixture of from about 10 to about 50 wt. % 2-mercapto-5-hydrocarbyldithio-1,3,4-thiadiazole 1,3,4-thiadazole and from about 50 to about 90 wt. % 2,5-bis (hydrocarbyldithio)-1,3,4-thiadiazole where the hydrocarbyl substituent of the thiadiazole are $C_1$ to $C_{30}$ alkyl. Most preferably, the hydrocarbyl is selected from the group consisting of heptyl, octyl, nonyl, decyl, undecyl, dodecyl, cetyl and isomers thereof.

The 1,3,4-thiadiazole compounds, or mixtures thereof, contemplated for use in the present invention can be readily obtained from commercial sources, such as the Amoco Petroleum Additives Company, or can be synthesized from hydrazine and carbon disulfide in a well-known manner. Particularly preferred for use in the invention are thiadiazole compositions commercially available from the Amoco Petroleum Additives Company under the trade names "Amoco-153" and "Amoco-158". U.S. Pat. Nos. 2,765,289; 2,749,311; 2,760,933; 2,850,453; 2,910,439; 3,6663,561; 3,862,798; and 3,840,549 may be referred to for detailed procedures on the preparation of the 1,3,4-thiadiazole compounds contemplated for use in lubricating compositions of the present invention. These patents are incorporated herein by reference.

The lubricating compositions of the present invention comprise a major amount of an oil of lubricating viscosity and a minor amount of at least one of the silver protective additives (A) through (C) or a synergistic combination of one of the additives (A) through (C) with an organo-sulfur compound as described above in amounts sufficient to provide silver lubricity in diesel engines having silver parts.

The oil of lubricating viscosity suitable for use in preparing the lubricant compositions of the present inventions can be of synthetic, animal, vegetable or mineral origin. Ordinarily, mineral lubricating oils are used by reason of their availability, general excellence, and low cost. Normally, the lubricating oils preferred will be fluid oils, ranging in viscosity of about 40 Saybolt universal seconds at 100° Fahrenheit to about 200 Saybolt universal seconds at 210° Fahrenheit. The preferred lubricant oil for use in the compositions of the present invention is a mineral base oil. The mineral base oil can be a blend of lubricant oils having viscosities such that the final viscosity at 100° Centigrade of the lubricating oil composition is preferably in the range of about 12.0 to 17.0 cSt. Thus, the suitable base lubricant mineral oil is selected to conform to viscosity requirements. The mineral base oil used to prepare the lubricating composition of the present invention preferably comprises a major portion, i.e., at least about 70 percent, and still more preferably, at least about 85 percent, by weight of the total composition.

In addition to a major proportion of mineral oil of lubricating viscosity, the lubricating compositions of the present inventions contain a minor amount of silver protective agents (A) through (C) or the combination of one or more of those agents with the organo-sulfur compounds discussed above. A minor amount of the silver protective agents prescribed for use in the present invention which is sufficient to provide silver protection in the lubricating compositions of the present invention is an amount that is within the range of about 0.001 wt. % to about 10 wt. %, based on the weight of the lubricating oil composition. Preferably, the amount is within the range of about 0.1 wt. % to about 7 wt. % and, more preferably, the amount is within the range of about 0.2 wt. % to about 1.0 wt. %, based on the weight of the lubricating oil composition.

Generally speaking, if the lubricant compositions of the present invention comprise the above-mentioned synergistic combination of said organo sulfur compounds and at least one member selected from the group consisting of silver protection agents (A) through (C), then a lesser amount of the agents would have to be used to achieve an equivalent amount of silver protection than would otherwise be required if either agents (A) through (C) were used alone or the organo-sulfur compounds were used alone. For example, it has been found that passing silver scar performance can be obtained in a lubricant composition comprising as the sole silver protection agent a 1,3,4-thiadiazole composition at a treat rate of about 0.7 weight percent of the lubricant composition. The same lubricating composition shows passing silver scar performance where the sole silver protection agent is oleyl aminotriazole present at a treat rate of about 0.6 weight percent. Surprisingly, however, the same lubricating composition containing only 0.2 weight percent of the thiadiazole in combination with 0.4 weight percent of the oleyl aminotriazole shows a markedly improved silver scar performance, indicating a true synergy between the thiadiazole and the oleyl aminotriazole as silver protection agents. A similar synergistic effect can be observed between the thiadiazole and the other silver protective ingredients (A) through (C) described earlier. In addition, the synergistic combination of 1,3,4-thiadiazole compounds and the silver protective ingredients (A) through (C) imparts to the lubricating compositions of the present invention a higher tolerance for overbased detergent additives, particularly phenates, which are ordinarily deleterious to silver parts.

In addition to the silver protection agents (A) through (C), or synergistic combinations thereof, with organo-sulfur compounds, the lubricating compositions of the present invention can contain additional additives to impart qualities considered necessary in a lubricating oil such as dispersancy, detergency, oxidation inhibition and foam inhibition.

A class of oil-soluble dispersants suitable for incorporation in the lubricating compositions of the present invention are the Mannich dispersants obtained from the condensation under Mannich reaction conditions of a hydroxyaromatic compound, aldehyde-yielding reagent, and amine. Preferred Mannich reactants are: (a) a high molecular weight alkyl-substituted hydroxyaromatic whose alkyl substituent has a number average molecular weight of about 600–100,000, preferably a polyalkylphenol whose polyalkyl substituent is derived from 1-mono-olefin polymers (preferably polybutene) having an Mn of about 850–2,500; (b) an amine containing at least one primary or secondary —NH group, preferably an alkylene polyamine selected from the group consisting of diethylenetriamine, triethylenetetraamine, tetraethylenepentaamine, or mixtures thereof; and (c) an aldehyde, preferably formaldehyde, paraformaldehyde or formalin. The preparation of Mannich base dispersants (borated and non-borated) is disclosed in Piasek, et al., U.S. Pat. Nos. 3,697,574; 3,703,536; 3,704,308; 3,751,365; 3,756,953; 3,798,165; 3,798,247; and 3,803,039, all of which are incorporated herein by reference.

A further class of oil-soluble dispersants suitable for incorporation in the lubricating compositions of the present invention are the carboxylic polyamine dispersants, more frequently termed "succinimides," given that the most prevalently used dispersant in this class is the reaction product of an alkenyl-substituted succinic acid or anhydride with a nitrogen-containing compound. The succinic dispersants that can be used in the present invention are disclosed in numerous references and have become exceedingly well known in the art. Examples are taught in U.S. Pat. Nos. 3,172,892; 3,219,666; and 3,272,746. If desired, borated succinic dispersants can also be used. See for example, U.S. Pat. Nos. 3,087,936 and 3,254,025. A preferred succinic dispersant for use in the present invention is the reaction product of a polybutenyl succinic anhydride, wherein the polybutenyl group has a number average molecular weight between about 700 and 5,000, and the polyethylenepolyamine is selected from the group consisting of diethylenetriamine, triethylenetetraamine, tetraethylenepentaamine, and mixtures thereof.

A further class of dispersants suitable for use in the present invention is the succinate ester-amide dispersants, the latter term denoting the reaction product a long-chain aliphatic hydrocarbyl-substituted succinic acid or anhydride with an N-substituted hydroxyalkylamine. Representative patents disclosing this type of ashless dispersant are Malec, U.S. Pat. No. 4,426,305; and LeSeur, U.S. Pat. Nos. 3,219,666, 3,640,904 and 3,282,955, all of which are incorporated by reference. Preferred succinate ester-amide dispersants suitable for use in the lubricating compositions of the present invention are prepared by reacting a polybutenyl succinic acid composition and an alkylene diamine, preferably hexamethylenediamine, said alkylene diamine having an average of at least about 2.5 N-hydroxyalkyl groups. If desired, the succinate ester-amides can be borated with boron oxide, boron dihalides, boron acids, etc.

Another class of dispersants suitable for use in the present invention comprise the reaction products of aliphatic or alicyclic halides containing at least about 40 carbon atoms with amines, preferably, polyalkylene polyamines, examples of which dispersants are described in U.S. Pat. Nos. 3,275,554; 3,438,757; 3,454,555; and 3,565,804; all of which are incorporated by reference.

Still another type of dispersant which can be used in the lubricating compositions of the present inventions are polymers containing an oil-solubilizing group, for example a pendant alkyl group having at least about 8 carbon atoms, and a polar group, for example, polymers of decyl methacrylate, vinyl decyl ether, or a relatively high molecular weight olefin with aminoalkyl acrylates, aminoalkyl acrylamides, or poly-(oxyalkalene)-substituted alkyl acrylates, as well as copolymers of styrene, alkyl maleates, and maleic acid amides or imides respectively. Such polymers can generally be identified as polymeric polyamine dispersants and are exemplified in U.S. Pat. Nos. 3,329,658; 3,449,250; 3,519,565; 3,666,730; 3,687,849; and 3,702,300, all of which are incorporated by reference.

In addition to the dispersant compositions described above, the lubricating compositions of the present invention also preferably include basic detergent additives providing a TBN (total base number) of at least about 7, and preferably, within the range of about 10 to about 30. Examples of components that are suitable for providing the required TBN in the additive composition of the present invention are overbased alkali or alkaline earth metal sulfonates, phenates and salicylates. The sulfonates are normal or basic metal salts of petroleum sulfonic acids or long-chain alkyl-substituted benzene sulfonic acids. The phenates are normal or basic salts of alkylphenols, alkylphenol sulfides, and alkylphenol-aldehyde condensation products. As is known in the art, a normal metal salt of an acid is a salt which contains the stoichiometric amount of metal required for the neutralization of the acidic group or groups present in the acid, while a basic salt or overbased salt is a salt which contains more metal than is required to stoichiometrically neutralize the acidic group or groups present. While both normal and overbased sulfonates and phenates provide detergent properties for lubricating oil compositions, the preferred overbased or superbasic or hyperbasic salts provide unusually high detergent power and, consequently, have a much greater capacity to neutralize acidic contaminants than do the normal sulfonates and phenates. As is well known in the art, overbased sulfonate is prepared by mixing a promoter, catalyst or solvent with a normal sulfonate and a larger excess of metallic base, followed by heating, carbonation and filtration. Carbonation of the reaction mass, accomplished conveniently with carbon dioxide, is employed to increase the amount of metal base colloidally dispersed as metal carbonate in the filtered product. Phenols, thioacids of phosphorous, alcoholates, alcohols, ketones, and alkanolamines can be used as promoters or catalysts. Typical metallic bases are basic compounds of alkali or alkaline earth metals, such as sodium calcium, barium or magnesium. Overbased metal detergents are discussed thoroughly in the prior art. Examples of such art are: U.S. Pat. Nos. 2,865,956; 2,956,018; 2,671,430; 3,779,920; 3,907,691; 4,137,184; 4,261,840; and 4,326,972. The overbased metal phenates are described in U.S. Pat. Nos. 2,680,096; 3,036,917; 3,178,368; 3,194,761; 3,437,595; 3,464,910; 3,779,920; and 4,518,807. All of the patents mentioned here are incorporated by reference. Numerous references also disclose methods of preparation for overbased salicylates.

A particularly preferred lubricating composition embodying the present invention has a TBN of at least 5 and comprises: (1) a major amount of an oil of lubricating viscosity; (2) from about 0.05 to about 1.0 weight percent of the silver protective agents, or synergistic combinations thereof, as set forth above; (3) from about 1 percent to about 10 weight percent of an ashless dispersant compound containing from about 40 weight percent to about 50 weight percent active component and selected from the group consisting of Mannich base dispersants, succinic dispersants, and succinate ester-amide dispersants; (4) from about 0 to about 20 weight percent alkali or alkaline earth metal detergent compositions to provide alkalinity reserve, oxidation inhibition and detergency to the lubricating oil composition, said alkaline earth metal compositions being selected from the group consisting of calcium alkylsulfonates, magnesium alkylsulfonates, sodium alkylsulfonates, calcium alkylphenolates, magnesium alkylphenolates, calcium alkylsalicylates, magnesium alkylsalicylates, and mixtures thereof.

A particularly preferred embodiment of the present invention is a lubricant composition comprising (1) a major proportion of mineral oil of lubricating viscosity; (2) a Mannich dispersant comprising the reaction product of alkylphenol, a polyamine and formaldehyde; (3) an alkaline earth metal salt of a Mannich condensation reaction product comprising the reaction product of alkylphenol, formaldehyde and a polyamine; (4) an alkylbenzene sulfonate of an alkaline earth metal; (5) an overbased alkaline earth metal phenate; (6) a silver protecting agent, or combination thereof, as described earlier; and (7) a small amount of a polydimethylsiloxane foam inhibitor.

The above embodiments can be prepared by suspending or dissolving in the mineral oil various additives. The mineral oil used can be selected to conform to viscosity requirements. Either a single base oil or blends of different viscosity base oils may be used as the base oil for the additive lubricant oil. The components may be blended in any order and in any combination. The first component of the preferred lubricant composition is the ashless dispersant, i.e., the Mannich condensation reaction obtained by reacting a polyalkylphenol, a polyamine and formaldehyde. The alkylphenol is commonly a high molecular weight alkyl-substituted hydroxyaromatic compound such as polypropyl phenol, polybutyl phenol or other alkylphenols. These alkylphenols may be obtained by the alkylation of phenol in the presence of an alkylating catalyst such as $BF_3$—HF, $BF_3$ or $AlCl_3$ with high molecular weight polypropene, polybutene or other polyalkene compounds to give alkyl substituents on the benzene ring of the phenol having a number average molecular weight of from about 600 to about 100,000. These alkyl-substituted hydroxyaromatic compounds may be derived from polypropenes, polybutenes and other polymers of monoolefins, principally 1-butene, 2-butene, isobutene and propene. Also, monomers may be copolymerized with propene or butene and other chlorinated, brominated or other derivatives of monoalkene compounds. The Mannich products may also contain fatty acids. The fatty acids compounds are thought to promote ease of production of the additives. The fatty acids also increase the detergency, the dispersancy and deposit preventing properties of the Mannich dispersants. Fatty acids such as oleic, linoleic, stearic and other $C_{16}$ to $C_{24}$ acids are suitable. Oleic acid is generally preferred. Preferably, the configuration of the alkyl-substituted hydroxyaromatic compound is that of para-alkylphenol. However, other alkylphenols are relatively reactive and thus useful in preparation of the Mannich dispersant. Representative amine reactants for use in preparing the Mannich dispersant preferred for use in the present invention are alkane polyamine, principally, polyethylene polyamines. Examples of amines which are useful are ethylamine, diethylamine, dimethylamine or propylamine; ethylenediamine, diethylenetriamine, triethylenetetraamine, tetraethylene pentaamine, pentaethylenehexamine, etc., and mixtures of the amines. Representative aldehydes for use in preparing the Mannich dispersant include paraformaldehyde, formalin, acetaldehyde, and betahydroxybutyraldehyde. Preferably a formaldehyde or formaldehyde-yielding reactant is used.

Component (3) prescribed for use in the preferred embodiment of the present invention is a low or high base alkylbenzene sulfonate. Such overbased alkylsulfonate is preferably produced from alkylated benzene sulfonic acid. The alkylated benzene sulfonic acid is generally produced by sulfonating benzene alkylates. The broad class of benzene alkylates include such compounds as polypropylbenzene, poly-1-butylbenzene, polyisobutylbenzene, poly-2-butylbenzene, polyethylenebenzene and copolymers of propyl and 1-butylbenzene and other various copolymers of ethylene, propene and butene isomers. The preferred alkylbenzenes are polypropyl, polybutyl and copolymer propylbutylbenzenes. Especially preferred are polypropylbenzenes wherein the alkyl moiety has a number average molecular weight of from about 400 to about 1,000. The alkaline metal salt which is used to overbase the alkylsulfonic acids may be chosen from a group consisting of barium oxide, calcium oxide, calcium hydroxide magnesium oxide or other group 1 and 2 metal bases. Preferably, the overbased sulfonic acids are produced from calcium oxide. The alkylbenzenes are commonly sulfonated with fuming sulfuric acid or oleum, in standard industrial sulfonation procedures. The sulfonate is overbased when the sulfonate contains more base than is needed to neutralize the sulfonic acid. Degrees of overbasing are measured in the form of total base number by ASTM D-2896. Total base number is equivalent to the milligrams of KOH equivalent to the amount of base in the composition which exceeds the amount needed to neutralize the sulfonic acids. TBN's of 1–400 are common.

Component (4) prescribed for use in the preferred embodiment of the present invention is the alkaline earth salt of an alkylphenol, formaldehyde, polyamine Mannich reaction product, preferably the calcium Mannich phenate. Phenols which have utility in this application are the alkylated phenols such as methyl, ethyl, propyl, butyl, pentyl, hexyl, heptyl, octyl, nonyl, decyl, undecyl, dodecyl, phenyl and the like. Also useful are alkylated phenols such as polyalkyl phenols formed from polyalkylenes and phenols. Formaldehyde may be in the form of paraformaldehyde, formalin or other well-known formaldehyde reactants. Polyamines such as ethylenediamine, diethylenetriamine, and tetraethylenepentaamine find utility in preparation of the calcium Mannich phenate. The Mannich condensation reaction product is overbased using an alkaline earth metal salt containing calcium, barium or magnesium to obtain a TBN of from about 1 to about 170. The metal may be in the form of oxides or hydroxides or carbonates. The preferred alkaline earth metal is calcium.

Component (5) prescribed for use in the preferred embodiment of the present invention is an overbased alkaline earth metal sulfurized alkylphenate sulfide used as an alkalinity agent/detergent. Alkylphenols such as decyl, nonyl, octyl or other phenols can be alkylated using polyalkylenes. The alkylphenols react with an alkali or alkaline earth metal such as sodium, calcium or magnesium to form a metal salt of an alkylphenate. TBN's from about 1 to about 300 may be obtained. A preferred alkaline earth metal salt of a sulfurized alkylphenate in the present invention is the high base sulfurized calcium phenate detergent available from the Amoco Petroleum Additives Company under the trade name "Amoco-9213".

Component (6) for use in the preferred embodiment of the present invention comprises the silver protective agents, or synergistic combinations thereof, as described in detail earlier.

Finally, Component (7) is preferably a silicon antifoam agent commonly used in the art and generally identified as a polydimethylsiloxane. The typical properties at 77° F. are viscosity in the range of about 10 to about 100,000 centistokes, pour point of about 40° F. to about 60° F., specific gravity of about 0.900 to about 0.995.

While it has been stated that additional additive agents may be incorporated in the lubricating compositions of the present invention, it is preferred that the lubricant composition of the present invention exclude zinc-containing wear agents if the lubricating compositions are used in diesel engines containing silver parts. This exclusion is intended to exclude amounts of zinc-containing wear inhibitors such as the zinc dihydrocarbyl dithiophosphate compounds sufficient to exert a measurable deleterious effect upon silver parts. At lesser amounts having no measurable effect, the lubricant is considered essentially free of zinc compounds for purposes of the present invention. If used in other engine or lubrication environments which do not contain silver parts, the additives of the present invention can provide useful lubricity, wear, and anti-corrosion properties and may be used in conjunction with zinc compounds. For example, the lubricating compositions of the present invention can be used in automatic transmission fluids where the inclusion of zinc-containing wear inhibitors may be desirable.

Insofar as the present invention provides effective substitutes for chlorine-containing silver lubricity agents, such as chlorinated paraffins, preferred embodiments of the lubricating compositions of the present invention are those excluding such agents.

The present invention is further illustrated by the following examples which are not, however, to be construed as limitations thereof.

EXAMPLE I

Preparation of Aminoguanidine Monooleamide

The reaction product of oleic acid and aminoguanidine bicarbonate useful as a silver protective agent in the lubricating composition of the present invention is prepared as follows: to a 5-liter, 3-neck flask was added oleic acid (847.5 g, 3 mols), aminoguanidine bicarbonate (408.33 g, 3 mols), 300 ml of toluene, and 15 drops of a silicon anti-foamant. The reaction mixture was heated to reflux under a nitrogen blanket. Vigorous foaming was noted as carbon dioxide gas evolved. When the foaming subsided, water evolution began. A total 57 ml of water was collected from the reaction by means of a Dean-Stark trap. The temperature of the reaction mixture was then raised to approximately 138° C. to facilitate the removal of toluene. To 1,040 g of the product, believed primarily to be oleyl amide of aminoguanidine, was added 1,040 g of process oil. The yellow oil solution was then filtered. Upon standing in air, this solution became red in color and had the following analysis: 3.83% nitrogen; activity, 50%; and Infra-red absorption ($cm^{-1}$) as follows: 3380–3040 (broad peak); 2920; 2850; 1665; 1530; 1465; and 1400.

EXAMPLE II

Preparation of Aminoguanidine Monooleamide

In a large reaction vessel was placed oleic acid (3,382 g, 11.97 mols), aminoguanidine bicarbonate (1,500 g of 90%, 9.92 mols), 5-W process oil (1,000 g) and a silicon anti-foamant (1 g). The mixture was stirred vigorously under nitrogen and heated to a temperature of 120° C. The aminoguanidine bicarbonate was observed to dissolve as the temperature of the reaction mixture neared 120° C. As the reaction progressed, carbon dioxide was evolved. The volume of the reaction mixture was expanded by approximately 40% due to foaming related to this gas evolution. Water was also evolved in the reaction. The reaction mixture was heated at 120° C. until a total of 308 ml of water collected. The mixture was then cooled and additional process oil was added sufficient to dilute the product to 50% activity. The final product had the following analysis: % Nitrogen, 7.02; Activity, 50%; viscosity (100° C., cSt), 19.11; TBN (mg KOH/g), 67.9; Infra-red absorbance, $mm^{-1}$ (1675 $cm^{-1}$, 24.9% in methyl cyclohexane), 8.57.

EXAMPLE III

Preparation of Dimer Acid Derivative of Aminoguanidine

Using the procedures of Example I, 141.3 g of a dimer acid, commercially available from Emery Industries, Cincinnati, Ohio, under the trade name "EMPOL 1010", was treated with 68.1 g of aminoguanidine bicarbonate in 125 ml of toluene. A total 9 ml of water was collected. The product (a yellow semi-solid) was not diluted with process oil. It had the following analysis: % nitrogen: 7.57; IR (neat) 3380–3000 (broad peak), 2940, 2870, 1675, 1535, 1465, 1400 ($cm^{-1}$); m.p. 50°–52° C.

EXAMPLE IV

Preparation Oleyl-1,2,4,-triazole

To a 1-liter, 3-neck flask was added oleic acid (282.5 g, 1 mol), aminoguanidine bicarbonate (136.11 g, 1 mol), and 100 ml of toluene. The mixture was slowly heated with stirring to reflux under a nitrogen blanket. Vigorous foaming was observed as carbon dioxide gas was evolved. Water evolution was also noted. Heating was continued until the water evolution ceased. Toluene was then removed by distillation. The temperature of the material remaining in the flask was allowed to rise to 182° C. and was held at that temperature for 3 hours. A steady stream of nitrogen gas was passed through the flask during this period to sweep out the water formed during this stage. The product was cooled to yield 274 g of a material believed to be the oleyl-1,2,4-triazole-3-amine product. This product solidified upon standing and had the following analysis: % nitrogen, 7.73; M.P: 55°–56° C.; IR: 3340–3040 (broad peak), 2930, 1690, 1640, 1600, 1550, 1450, 1380, 1070, and 725 ($cm^{-1}$).

EXAMPLE V

Triazole Preparation Using Dimer Acid

Using the procedures of Example IV, 141.3 g dimer acid ("EMPOL 1010") was treated with 68.1 g of aminoguanidine bicarbonate in 125 ml of toluene. The water of reaction (approximately 6 ml) was removed from the reaction mixture as a toluene azeotrope. The toluene in turn was removed from the reaction mixture using vacuum distillation (at about 18 mm of mercury). The residue was heated to 182° C. and held at that temperature for 3 hours. During this period, 7 ml of additional water was collected. The product was not diluted with process oil. It had the following analysis: % Nitrogen, 7.67; M.P. 73° C.

EXAMPLE VI

Using the procedures of Example I, with the exception that no diluent oil was used, aminoguanidine monooleamides were prepared by varying the oleic acid to aminoguanidine bicarbonate (AGB) ratio, as follows:

| Moles Oleic Acid | Moles AGB | Ml of $H_2O$ Collected | Product Yield (g) | % N | TBN | M.P. (°C.) |
|---|---|---|---|---|---|---|
| 0.34 | .33 | 10 | 105 | 8.06 | 144.8 | 55 |
| 0.36 | .33 | 4 | 108.5 | 7.72 | 140.2 | 53 |
| 0.39 | .33 | 7 | 125.6 | 7.13 | 126.9 | 37 |
| 0.46 | .33 | 3 | 106.5 | 6.48 | 118.2 | 34 |

EXAMPLE VII

SILVER LUBRICITY BENCH TEST RESULTS

Lubricant compositions of the present invention containing no chlorinated compounds and no zinc-containing compounds were bench tested for their ability to protect against silver scarring. In the test, which is well known in the art, a polished steel ball is rotated against a trio of silver discs immersed in the test oil in a heated holder while a fixed load is applied. After thirty minutes, the test is stopped, the discs removed, and the wear scar made by the steel ball on each disc is measured. (For purposes of comparison, it should be pointed out that prior art railway diesel engine oils containing chlorinated silver lubricity agents usually produce a wear scar of 1.3 mm to 1.8 mm in diameter, which is considered acceptable.)

Except for varying the type and amount of silver protective agent used, the lubricant formulation used in this Example was as follows:

| Component | Wt. % |
|---|---|
| Mannich Dispersant | 3.3 |
| Calcium Mannich Phenate | 4.8 |
| Calcium Sulfonate | 2.0 |
| Calcium Sulfurized Phenate | 1.65 |
| Amoco SX-5 | 0.2 |
| Mid-Range Viscosity | |
| Index Base Oil | Remainder |
| Silver Lubricity Agent | 0.5–.70 |

Blends 1 to 6 below used the above formulation and contained, as the silver lubricity agent, either a 1,3,4-thiadiazole compound (Amoco "A-158"), an oleyl aminotriazole (Example IV) or a synergistic combination of the two:

| Blend | Wt. % Thiadiazole | Wt. % Oleyl Aminotriazole | Silver Scar (Pass <1.9) |
|---|---|---|---|
| 1 | 0.10 | 0.0 | 1.9 |
| 2 | 0.50 | 0.0 | 1.6 |
| 3 | 0.00 | 0.6 | 1.8 |
| 4 | 0.10 | 0.2 | 1.7 |
| 5 | 0.10 | 0.6 | 1.1 |
| 6 | 0.20 | 0.4 | 1.2 |

Blends 7 to 12 below contained either a 1,3,4-thiadiazole compound ("A-158"), an aminoguanidine monooleamide (Example I), or a synergistic combination of the two:

| Blend | Wt. % Thiadiazole | Wt. % Aminoguanidine Monooleamide | Silver Scar <1.9 = Pass |
|---|---|---|---|
| 7 | 0.00 | 0.20 | 2.7 |
| 8 | 0.00 | 0.25 | 2.6 |
| 9 | 0.00 | 0.30 | 1.3 |
| 10 | 0.00 | 0.20 | 1.1 |
| 11 | 0.10 | 0.20 | 1.3 |
| 12 | 0.10 | 0.30 | 1.1 |

The results of this Example demonstrate: (1) that aminoguanidine monooleamide, by itself, is an effective silver lubricity agent in a formulation containing no chlorine compounds; (2) that oleyl aminotriazole, by itself, is an effective silver lubricity agent; (3) that 1,3,4-thiadiazole compounds, by themselves, have silver lubricity properties; and (4) a synergistic effect is achieved by combining 1,3,4-thiadiazoles with either the aminoguanidine monooleamide or the oleyl aminotriazole (Blends 4 to 6, 11, and 12).

EXAMPLE VIII

The surprising effectiveness of the lubricant compositions of the present invention, as compared to those utilizing the prior art chlorinated compounds, is demonstrated in this example. In particular, it is shown that a lubricating composition containing twice the amount of overbased calcium phenate as that used in the formulation of Example XII (i.e., 3.15 wt. % versus 1.65 wt. %) can pass the silver scar bench test at relatively low levels of the synergistic silver protective agent combinations prescribed for use in the present invention, while higher levels of the chlorinated silver protective agents excluded from the present invention are substantially inferior.

The formulation tested in the present example was as follows:

| Component | Wt. % |
|---|---|
| Mannich Dispersant | 3.3 |
| Calcium Mannich Phenate | 2.3 |
| Calcium Sulfonate | 2.0 |
| Calcium Sulfurized Phenate | 3.15 |
| Mid-Range Viscosity | |
| Index Base Oil | Remainder |
| Silver Lubricity Agent | .4–.9 |

A total of 9 blends were examined by varying the type and amount of silver lubricity agent used in the above formulation. Blends 1 to 3 are comparative runs using silver lubricity agents not encompassed by the present invention Runs 4 to 9 are in accordance with the present invention and use synergistic combinations of thiadiazole compounds ("Amoco-158" or "Amoco-153" available from Amoco Petroleum Additives Company) with either aminoguanidine monooleamide ("AGMO") or a commercially-obtained imidazoline compound obtained from Ciba-Geigy under the trade name "Amine O".

| Blend | Silver Lubricity Agent(s) (wt. %) | Silver Scar (Pass = <1.9) |
|---|---|---|
| 1 | 0.30 A-158 + 0.30 Chlorowax-40 | 3.1 |
| 2 | 0.80 Chlorowax-40 + 0.60 1,2,4-triazole | 2.5 |
| 3 | 0.09 Chlorowax-40 + 0.40 fatty acid partial ester | 2.9 |
| 4 | 0.10 Amoco-158 + 0.30 AGMO | 1.3 |
| 5 | 0.05 Amoco-158 + 0.35 AGMO | 1.5 |
| 6 | 0.15 Amoco-153 + 0.30 AGMO | 1.6 |
| 7 | 0.05 Amoco-153 + 0.35 AGMO | 1.8 |
| 8 | 0.30 Amoco-158 + 0.60 Amine O | 1.8 |
| 9 | 0.15 Amoco-153 + 0.40 Amine O | 1.6 |

EXAMPLE IX

A formulation containing an even higher level of phenate detergent than that used in Example XIII was tested in the following formulation:

| Component | Wt. % |
|---|---|
| Mannich Dispersant | 1.7 |
| Calcium Mannich Phenate | 2.3 |
| Calcium Sulfonate | 2.0 |
| Calcium Sulfurized Phenate | 3.5 |
| Base Oil | Remainder |
| Silver Lubricity Agent | * |

*0.20 0.20 wt. % A-158 plus 0.50 wt. % of a reaction product of oleic acid and N-methyl glycine obtained from Ciba-Geigy under the trade name "Sarcosyl O".

The bench test results showed a silver scar of 1.7 (<1.9 is passing) which is excellent in view of the results obtained for Blends 1, 2, and 3 in the preceding example.

We claim:

1. An internal combustion engine lubricating composition comprising a major proportion of an oil of lubricating viscosity and (1) a minor amount of a silver-protective additive composition comprising the reaction product of a $C_5$ to $C_{60}$ carboxylic acid and at least one amine selected from the group consisting of (i) guanidine, urea and thiourea compounds; (ii) $C_1$ to $C_{20}$ hydrocarbyl or hydroxy-substituted hydrocarbyl (a) mono-amines, (b) alkylene diamines, and (c) polyalkylene polyamines; and (iii) N-alkyl glycine; (2) a minor amount, effective for dispersancy, of an ashless dispersant; and (3) a minor amount, effective for detergency, of at least one detergent selected from the group consisting of alkali and alkaline earth metal sulfonates, phenates and salicylates.

2. An internal combustion engine lubricating composition comprising a major proportion of an oil of lubricating viscosity and (1) a minor amount of a silver protective additive composition comprising at least one member selected from the group consisting of:
   (A) the reaction product of a $C_5$ to $C_{60}$ carboxylic acid and
      (i) compounds having the general formula:

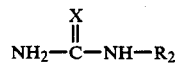

wherein X is $NR_1$, O, or S, and $R_1$ is H or $C_1$ to $C_{15}$ hydrocarbyl and $R_2$ is H, —NR'R", or $C_1$ to $C_{20}$ hydrocarbyl or hydroxy-substituted hydrocarbyl and R' and R" (being the same or different) are H or $C_1$ to $C_{20}$ hydrocarbyl or hydroxy-substituted hydrocarbyl;
   or (ii) salts of said compounds;
   (B) the reaction product of a $C_5$ to $C_{60}$ carboxylic acid and at least one amine selected from the group consisting of (i) mono-amines having the formula HNRR' where R and R' (being the same or different but not both H) are H or $C_1$ to $C_{20}$ hydrocarbyl or hydroxy-substituted hydrocarbyl; and (ii) alkylene diamines having the general formula:

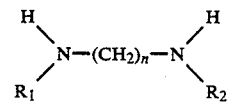

wherein n=2 to 10, and $R_1$ and $R_2$ (being the same or different) are H or $C_1$ to $C_{20}$ hydrocarbyl or hydroxy-substituted hydrocarbyl; and (iii) polyalkylene polyamines having the general formula:

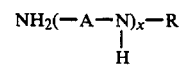

wherein A is a divalent alkylene radical having 2 to 6 carbon atoms; x is an integer from 1 to 10; and R is H or $C_1$ to $C_{20}$ hydrocarbyl or hydroxy-substituted hydrocarbyl;
   (C) the reaction product of a $C_5$ to $C_{60}$ carboxylic acid and derivatives of glycine having the general formula:

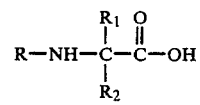

wherein R is H or $C_1$ to $C_{20}$ hydrocarbyl or hydroxy-substituted hydrocarbyl; and R' and R" being the same or different are H or $C_1$ to $C_{20}$ hydrocarbyl; (2) a minor amount, effective for dispersancy, of an ashless dispersant; and (3) a minor amount, effective for detergency, of at least one detergent selected from the group consisting of alkali and alkaline earth metal sulfonates, phenates and salicylates.

3. The lubricating composition of claim 2 wherein the oil is a mineral oil.

4. The lubricating composition of claim 2 wherein the oil is a synthetic oil.

5. The lubricating compositions of claim 3 comprising silver protective additive (A), said additive being obtained by reacting a $C_{16}$ to $C_{26}$ fatty acid with a salt of aminoguanidine under reaction conditions giving rise predominantly to an amide.

6. The lubricating composition of claim 5 wherein silver protective additive (A) is obtained by reacting oleic acid and aminoguanidine bicarbonate under reaction conditions giving rise predominantly to aminoguanidine monooleamide having either of the following formulae where R is the remainder of the oleyl substituent of the amide:

$$\underset{R-NH-C-NH-NH_2}{\overset{NH}{\|}}$$

$$\underset{R-NH-NH-C-NH_2}{\overset{NH}{\|}}.$$

7. The lubricating composition of claim 6 wherein said reaction conditions comprise a temperature in the range of from about 100° C. to about 150° C.

8. The lubricating composition of claim 7 wherein said reaction conditions comprise a temperature in the range of from about 120° C. to about 145° C., and the mole ratio of oleic acid to aminoguanidine bicarbonate is about 0.8:1 to about 1.2:1.

9. The lubricating composition of claim 8 which is essentially free of chlorine-containing silver lubricity agents and zinc-containing wear agents.

10. The lubricating composition of claim 5 wherein the silver protective additive (A) is obtained by reacting oleic acid and aminoguanidine bicarbonate under reaction conditions giving rise predominantly to a triazole comprising 1,2,4-triazole-3-amine having the following formula:

$$CH_3(CH_2)_7CH=CH(CH_2)\underset{N}{\overset{N-----N}{\diagup\diagdown}}NH_2.$$

11. The lubricating composition of claim 10 wherein the reaction conditions comprise a reaction temperature of from about 175° C. to about 200° C.

12. The lubricating composition of claim 11 which is essentially free of chlorine-containing silver lubricity agents and zinc-containing wear agents.

13. The lubricating composition of claim 3 comprising silver protective additive agent (B) wherein said additive is obtained by reacting said carboxylic acid with an alkylene diamine.

14. The lubricating composition of claim 13 wherein the alkylene diamine is ethylene diamine and the reaction product comprises an imidazoline having the formula where R represents the remainder of the carboxyl moiety:

$$R-C\underset{\underset{H}{N}}{\overset{N}{\diagup\diagdown}}\underset{C}{\overset{C}{|}}$$

15. The lubricating composition of claim 3 comprising silver protective additive (B), said additive being a commercial imidazoline product sold under the trade name "Amine O".

16. The lubricating composition of claim 15 which is essentially free of chlorine-containing silver lubricity agents and zinc-containing wear agents.

17. The lubricating composition of claim 3 comprising silver protective additive (C) wherein said additive is obtained by reacting said carboxylic acid with N-methyl glycine.

18. The lubricating composition of claim 17 comprising the silver protective additive (C), said additive comprising an amide having the following structure where R represents the remainder of the carboxylic acid moiety:

$$\underset{R-N-CH_2-C-OH.}{\overset{CH_3}{\underset{|}{\phantom{M}}}\phantom{-CH_2-}\overset{O}{\|}}$$

19. The lubricating composition of claim 17 comprising silver protective additive (C) wherein said additive is the commercial product sold under the trade name "Sarkosyl O".

20. The lubricating composition of claim 17 which is essentially fre of chlorine-containing silver lubricity agents and zinc-containing wear agents.

21. A method for protecting silver engine parts in an internal combustion engine which method comprises the step of contacting the internal portion of said engine with a lubricating composition comprising a major proportion of an oil of lubricating viscosity and a minor amount of a silver protective additive composition comprising the reaction product of a $C_5$ to $C_{60}$ carboxylic acid and at least one amine selected from the group consisting of (i) guanidine, urea or thiourea compounds; (ii) $C_1$ to $C_{20}$ hydrocarbyl or hydroxy-substituted hydrocarbyl (a) mono-amines, (b) alkylene diamines, and (c) polyalkylene polyamines; and (iii) N-alkyl glycine.

22. A method for protecting silver engine parts in an internal combustion engine which method comprises the step of contacting the internal portion of said engine with a lubricating composition comprising a major proportion of an oil of lubricating viscosity and a minor amount of a silver protective additive comprising at least one member selected from the group consisting of:

(A) the reaction product of a $C_5$ to $C_{60}$ carboxylic acid and (i) compounds having the general formula:

$$\underset{NH_2-C-NH-R_2}{\overset{X}{\|}}$$

wherein X is $NR_1$, O, or S; where $R_1$ is H or $C_1$ to $C_{15}$ hydrocarbyl and $R_2$ is H, or —NR'R', or $C_1$ to $C_{20}$ hydrocarbyl or hydroxy-substituted hydrocarbyl and R' and R" (being the same or different) are H or $C_1$ to $C_{20}$ hydrocarbyl or hydroxy-substituted hydrocarbyl;

or (ii) salts of said compounds;

(B) the reaction product of a $C_5$ to $C_{60}$ carboxylic acid and at least one amine selected from the group consisting of (i) mono-amines having the formula HNR'R" where R' and R" (being the same or different but not both H) are H or $C_1$ to $C_{20}$ hydrocarbyl or hydroxy-substituted hydrocarbyl; and (ii) alkylene diamines having the general formula:

$$\underset{R_1}{\overset{H}{\diagdown}}N-(CH_2)_n-N\underset{R_2}{\overset{H}{\diagup}}$$

wherein n=2 to 10, and $R_1$ and $R_2$ (being the same or different) are H or $C_1$ to $C_{20}$ hydrocarbyl or hydroxy-substituted hydrocarbyl; and (iii) polyalkylene polyamines having the general formula:

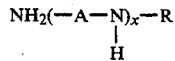

wherein A is a divalent alkylene radical having 2 to 6 carbon atoms; X is an integer from 1 to 10; and R is H or $C_1$ to $C_{20}$ hydrocarbyl or hydroxy-substituted hydrocarbyl;

(C) the reaction product of a $C_5$ to $C_{60}$ carboxylic acid with derivatives of glycine having the general formula:

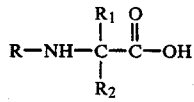

wherein R is H or $C_1$ to $C_{20}$ hydrocarbyl or hydroxy-substituted hydrocarbyl; and R' and R" (the same or different) are H or $C_1$ to $C_{20}$ hydrocarbyl.

23. The method of claim 21 wherein the silver protective additive is (A) said additive being obtained by reacting oleic acid and aminoguanidine bicarbonate at a temperature in the range of from about 100° C. to about 150° C. to form a product comprising a major proportion of aminoguanidine monooleamide having either of the following formulae:

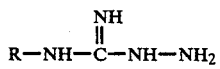

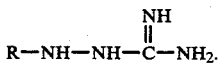

24. The method of claim 23 wherein the lubricating composition further comprises an ashless dispersant and an overbased alkali or alkaline earth metal sulfonate, phenate or salicylate.

25. The method of claim 22 the silver protective additive is (A) said additive being obtained by reacting oleic acid and aminoguanidine bicarbonate at a temperature in the range of about 170° C. to 200° C. giving rise predominantly to a triazole having the following formula where R is the remainder of the oleyl substituent.

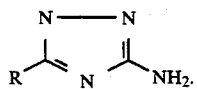

26. The method of claim 25 wherein the lubricating composition further comprises an ashless dispersant and an overbased alkali or alkaline earth metal sulfonate, phenate or salicylate.

27. The method of claim 22 wherein the silver protective additive is (B) obtained by reacting the carboxylic acid with ethylene diamine to obtain a reaction product comprising predominantly an imidazoline having the formula where R is the remainder of the carboxyl substituent.

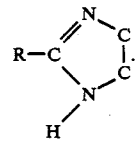

28. The method of claim 27 wherein the lubricating composition further comprises an ashless dispersant and an overbased alkali or alkaline earth metal sulfonate, phenate or salicylate.

29. The method of claim 22 the silver protective additive is (C) obtained by reacting the carboxylic acid with N-methylglycine to obtain a reaction product comprising predominantly an amide having the following formula in which R represents the remainder of the carboxylic acid moiety:

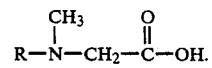

30. The method of claim 22 wherein the silver protective additive further comprises a thiadiazole compound having the general formula:

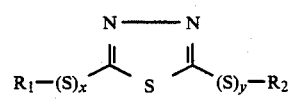

where x and y (being the same or different) are integers from 1 to 5 and $R_1$ and $R_2$ (being the same or different) are H or $C_1$ to $C_{50}$ hydrocarbyl.

31. The method of claim 30 wherein the thiadiazole is a mixture comprising about 50 to about 90 wt. % of 2,5-bis-(hydrocarbyldithio)-1,3,4-thiadiazole and about 10 to about 50 wt. % of 2-mercapto-5-(hydrocarbyldithio)-1,3,4-thiadiazole wherein the hydrocarbyl is $C_1$ to $C_{20}$ alkyl.

32. The method of claim 31 wherein the hydrocarbyl moiety is selected from the group consisting of heptyl, octyl, nonyl, decyl, undecyl, dodecyl, cetyl and isomers thereof.

33. The method of claim 32 wherein the lubricating composition further comprises an ashless dispersant and an overbased alkali or alkaline earth metal sulfonate, phenate or salicylate.

* * * * *